United States Patent [19]
Kleinschroth et al.

[11] Patent Number: 4,681,885
[45] Date of Patent: Jul. 21, 1987

[54] 5-OXO-PYRIDO[4,3-]PYRIMIDINE DERIVATIVES

[75] Inventors: Jürgen Kleinschroth, Denzlingen; Karl Mannhardt, Elzach-Oberprechtal; Johannes Hartenstein, Stegen-Wittental; Hartmut Osswald, Waldkirch; Bernd Wagner, Denzlingen, all of Fed. Rep. of Germany

[73] Assignee: Godecke Aktiengesellschaft, Berlin, Fed. Rep. of Germany

[21] Appl. No.: 819,958

[22] Filed: Jan. 21, 1986

[30] Foreign Application Priority Data

Jan. 28, 1985 [DE] Fed. Rep. of Germany ....... 3502742

[51] Int. Cl.⁴ .................. A61K 31/505; C07D 487/04
[52] U.S. Cl. .................................... 514/258; 544/279
[58] Field of Search ........................ 544/279; 514/258

[56] References Cited

FOREIGN PATENT DOCUMENTS 1050982  3/1986  Japan ................................. 544/279

Primary Examiner—Mark L. Berch
Assistant Examiner—Barbara Cassatt
Attorney, Agent, or Firm—Elizabeth M. Anderson

[57] ABSTRACT

The invention concerns new 5-oxo-pyrido[4,3-d]pyrimidine derivatives and the pharmacologically acceptable salts thereof, as well as a chemically novel process for the preparation of the new compounds and their use in the control of cerebral, cardiac, or peripheral vascular diseases or of stenotic symptoms.

5 Claims, No Drawings

5-OXO-PYRIDO[4,3-]PYRIMIDINE DERIVATIVES

SUMMARY OF THE INVENTION

The invention concerns new 5-oxo-pyrido[4,3-d]-pyrimidine derivatives of the general Formula Ia

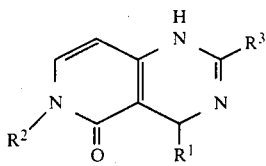
(Ia)

or their tautomeric forms of the general Formulae Ib and Ic

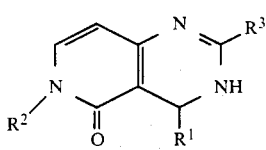
(Ib)

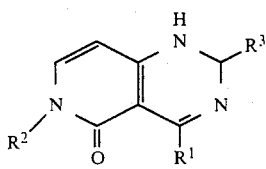
(Ic)

or tautomeric mixtures thereof, wherein $R^1$ represents an unsubstituted or substituted phenyl radical;

$R^2$ is hydrogen, an alkyl, alkoxyalkyl;, or substituted or unsubstituted aminoalkyl group with up to ten carbon atoms; and $R^3$ is a straight or branched alkyl group with up to four carbon atoms or an unsubstituted or substituted phenyl radical;

as well as optionally the pharmacologically acceptable acid addition salts thereof.

The invention also includes a pharmaceutical composition comprising an effective amount of a compound described above together with a pharmacologically acceptable carrier or diluent.

The invention further includes a method of treating vascular diseases comprising administering to a host suffering therefrom an effective amount of a compound described above in unit dosage form.

DETAILED DESCRIPTION

Substituents on the phenyl radical comprise one or more of the same or different groups such as halogen, e.g. fluorine, chlorine, bromine or iodine, nitro, $C_1$–$C_4$ alkyl, e.g., methyl, $C_1$–$C_4$ alkoxy, e.g., methoxy, difluoromethoxy, trifluoromethoxy, dimethylamino or diethylamino, methylthio or trifluoromethyl, or methylenedioxy.

Alkyl or alkoxy refer to straight or branched hydrocarbon atoms which, unless otherwise designated, have up to six carbon atoms.

Substituted aminoalkyl refers to alkyl or dialkylaminoalkyl groups or alkyleneaminoalkyl which form four to seven membered rings, but preferably five or six membered rings with the nitrogen atom.

Preferred are compounds of the Formulae Ia, Ib, and Ic wherein $R^1$ represent phenyl or phenyl substituted in the two and/or three or six position;

$R^2$ is $C_1$–$C_6$ alkyl group, a $C_1$–$C_8$ alkoxyalkyl group, or a $C_1$–$C_8$ aminoalkyl group; and $R^3$ is a $C_1$–$C_6$ alkyl or a phenyl radical.

Especially preferred are 5-oxo-pyrido[4,3-d]-pyrimidine derivatives of the general Formulae Ia, Ib, and Ic, wherein $R^1$ represents phenyl or phenyl substituted, preferably in the two or three position, by halogen, nitro, methyl, methoxy, difluoromethoxy, trifluoromethoxy, dimethylamino, diethylamino, methylthio or trifluoromethyl, or phenyl disubstituted, preferably in the 2,3 position, by methoxy or methylenedioxy, or in the 2,3 or 2,6 position by halogen atoms, which may be the same or different;

$R^2$ is a methyl, ethyl, n-propyl, isopropyl, n-butyl, isobutyl or tert. butyl radical, an alkoxyalkyl group of the general Formula II

$$-(CH_2)_n-O-R^4 \qquad (II)$$

or an aminoalkyl group of the general Formula III

(III)

wherein $R^4$ represents a straight or branched alkyl group and $R^5$ and $R^6$ may be the same or different and represent a straight or branched alkyl group, or together form an alkylene group, and n equals two or three, and $R^3$ represents a methyl, ethyl, n-propyl, isopropyl, or phenyl radical or phenyl substituted as for $R^1$ above.

The compounds of the present invention may be prepared by a process via intermediate products of the general Formula IVa

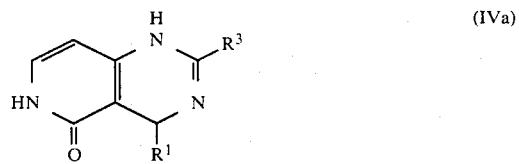
(IVa)

or IVb and IVc

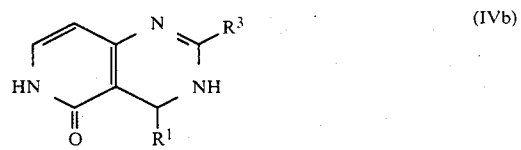
(IVb)

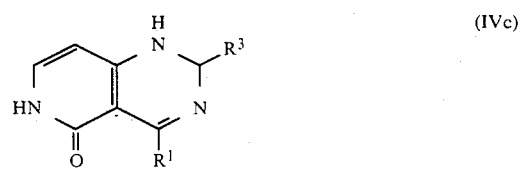
(IVc)

or tautomeric mixtures thereof, wherein $R^1$ and $R^3$ have the above stated meaning. The compounds of the general Formulae Ia, or Ib and Ic, are obtained by alkylating, aminoalkylating or alkoxyalkylating compounds of the general Formulae IVa, or IVb and IVc, in a previously known manner.

The compounds of the general Formulae IVa, IVb, and Ivc, are prepared by reacting with s-triazine in the presence of a base dihydropyrimidines of the general Formulae Va

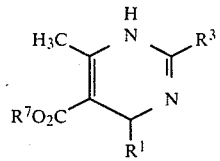

(Va)

or Vb and Vc

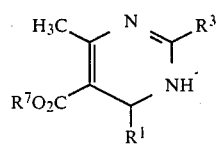

(Vb)

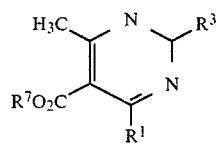

(Vc)

or compounds consisting of tautomeric mixtures thereof, in which $R^1$ and $R^3$ have the above meaning, and $R^7$ represents a methyl or ethyl group. So far this reaction has not been known and has been unforeseeable as to its progress.

The compounds of the general Formulae Ia, or Ib and Ic, are prepared in a generally known manner by alkylation, or aminoalkylation or alkoxyalkylation, of the compounds of the general Formulae IVa, IVb and IVc, with compounds of the general Formula VI $$X \text{—} R^2 \qquad (VI)$$

in which $R^2$ has the above meaning and X represents a halogen, in particular chlorine, bromine, or iodine, preferably in the presence of a hydrohalogenide acceptor, e.g., triethylamine of pyridine.

The compounds of the general Formulae Va, or Vb and Vc, are known from the literature (German patent application No. 32 34 684) or can be prepared analogously.

The reaction is performed by heating to temperatures of 50°–160° C., preferably 100°–150° C., the dihydropyrimidine derivative together with s-triazine in an inert organic solvent. Suitable solvents are mainly polar solvents such as dimethyl sulfoxide, dimethylformamide, or ethylene glycol dimethyl ether.

The alkylation, aminoalkylation, and alkoxyalkylation of the compounds of the general Formulae IVa, or IVb and IVc, is performed according to generally known methods, preferably using a hydro-halogenide acceptor. If suitable conditions are chosen for the reaction its course shows a high regional selectivity. The O-alkylation products to be expected are surprisingly formed only in low quantities. The products are separated and purified by means of chromatography and/or crystallization.

Dependent on the substituents $R^1$ and $R^3$ the compounds of the general Formulae Ia, or Ib and Ic, are of a more or less basic character at the pyrimidine ring and are therefore, for purification purposes and pharmaco-technological reasons, preferably converted to pharmacologically acceptable crystalline salts; the same applies to compounds of the general Formulae Ia, or Ib and Ic, in which $R^2$ represents a substituted or unsubstituted aminoalkyl group. These salts are obtained in the usual manner by neutralizing the bases with the corresponding inorganic or organic acids. As acids may be used, e.g., hydrochloric acid, sulfuric acid, phosphoric acid, hydrobromic acid, acetic acid, tartaric acid, lactic acid, citric acid, malic acid, salicyclic acid, ascorbic acid, malonic acid, or succinic acid.

Since the compound of the general Formulae Ia, or Ib and Ic, according to the invention show a *chiral* center either at C-2 or at C-4, they can be present either as racemic mixtures or in the form of enantiomers. The present invention includes both mixtures and enantiomers.

Being calcium antagonists the compounds of the general Formulae Ia, or Ib and Ic, exert vasospasmolytic, vasodilatory, and antihypertensive activities.

For reason of their vasospasmolytic effects the compounds are mainly indicated for the treatment of cerebral, cardiac, and peripheral vascular diseases such as myocardial ischemia, cerebral infarction, pulmonary thromboses, as well as in cases of arteriosclerosis and other stenotic symptoms. The 5-oxo-pyrido[4,3-d]pyrimidine derivatives of the present invention are therefore valuable agents for combating cardiovascular mortality. Another subject matter of the present invention is therefore, the use of the 5-oxo-pyrido[4,3-d]pyrimidines of the general Formulae Ia, or Ib and Ic, in the control of vascular diseases.

The compounds of the general Formulae Ia, or Ib and Ic, according to the invention may be applied in liquid or solid form, orally or parenterally. For the injection-solution mainly water is used containing such additives as stabilizers, solubilizers, or buffers as are usual for injection-solutions.

Such additives are, e.g., tartrate and citrate buffers, ethanol, complex formers (such as ethylenediamine tetraacetic acid and the nontoxic salts thereof), as well as high molecular weight polymers (such as liquid polyethylene oxide) to regulate the viscosity. Solid vehicles are, e.g., starch, lactose, mannitol, methyl cellulose, talc, highly dispersed silicic acids, higher molecular weight fatty acids (such as stearic acid), gelatin, agar-agar, calcium phosphate, magnesium stearate, animal and vegetable fats, solid high molecular weight polymers (such as polyethylene glycol); if desired preparations suited for oral application may in addition contain flavors and/or sweetening agents.

Enterally administered single doses are in the order of about 5 to 250 mg, preferably 10 to 100 mg. Doses for parenteral application are from about 1 to 20 mg.

Since the compounds of the present invention exist in three possible tautomeric forms or in equilibrium among the three forms, the invention as claimed contemplates the three forms and equilibrium mixtures thereof. For simplicity sake, only one form has been illustrated in the claims.

The following examples serve to further illustrate the invention.

EXAMPLE 1

±-4-(3-Chlorophenyl)-1,4,5,6-tetrahydro-5-oxo-2-phenyl-pyrido[4,3-d]pyrimidine

To a stirred suspension of 6.0 g (0.20 mol) sodium hydride (80% in oil) in 100 ml dry dimethylformamide, and in nitrogen atmosphere, is added dropwise a solution of 46.4 g (0.14 mol) (±)-4-(3-chlorophenyl)-1,4-dihydro-6-methyl-2-phenyl-pyrimidine-5-carboxylic acid methyl ester (German patent application No. 32 34 684) in 300 ml dimethylformamide. When the gas generation diminishes stirring is continued at room temperature for 30 minutes; subsequently 11.3 g (0.14 ml) s-triazine in 200 mmol dimethylformamide are added dropwise. The reaction mixture is heated to 100°–110° C. for 16 hours and reduced under vacuum when cool. The dark residue is treated with one liter acetone in the supersonic bath, and filtered off from the undissolved matter. The acetone solution is evaporated under vacuum and the residue subjected to chromatography on silica gel with dichloromethane/methanol (9:1). The fraction of the $R_f$ 0.45 is isolated and recrystallized from methanol.

This process yields (±)-4-(3-chlorophenyl)-1,4,5,6-tetrahydro-5-oxo-2-phenyl-pyrido[4,3-d]-pyrimidine in the form of light beige crystals with a m.p. of 172°–173° C.

The following compounds are prepared analogously:
(±)-1,4,5,6-Tetrahydro-4-(3-nitrophenyl)-5-oxo-2-phenyl-pyrido[4,3-d]pyrimidine (1.a)
  m.p. 206°–207° C. from methylene chloride.
(±)-1,4,5,6-Tetrahydro-2-methyl-5-oxo-4-phenyl-pyrido[4,3-d]pyrimidine (1.b)
  m.p. 263°–264° C. from ethyl acetate/methanol.
(±)-1,4,5,6-Tetrahydro-2-methyl-5-oxo-4-(2-trifluoromethyl-phenyl)-pyrido[4,3-d]pyrimidine (1.c)
(±)-1,4,5,6-Tetrahydro-2-methyl-4-(2-nitrophenyl)-oxo-pyrido[4,3-d]pyrimidine (1.d)
(±)-1,4,5,6-Tetrahydro-2-(3-nitrophenyl)-5-oxo-4-(2-trifluoro-methylphenyl)-pyrido[4,3-d]pyrimidine (1.e)

EXAMPLE 2

(±)-1,4,5,6-Tetrahydro-6-isopropyl-2-methyl-5-oxo-4-phenyl-pyrido[4,3-d]pyrimidine hydrochloride To a stirred suspension of 1.24 g (41.3 mmol) sodium hydride (80% in oil) in 50 ml dry dimethyl-formamide are added in portions 8.97 g (37.5 mmol) (±)-1,4,5,6-tetrahydro-2-methyl-5-oxo-4-phenyl-pyrido-[4,3-d]pyrimidine in solid form. When the gas generation diminishes stirring at room temperature is continued for 30 minutes; subsequently 9.56 g (56.2 mmol) isopropyl iodide in 20 ml dimethylformamide are added dropwise.

Stirring is continued at room temperature for 72 hours, the solvent distilled off under vacuum, and the residue mixed with 100 ml water by stirring. The water is decanted, the residue dissolved in dichloromethane and the solution washed again with water. The dichloromethane solution is dried over sodium sulfate and evaporated under vacuum. The residue is subjected to chromatography on silica gel with ethyl acetate/methanol, NH₃ sat. 95:5.

The fraction of the $R_f$ 0.1 is dissolved in ether/ethyl acetate and converted into the hydrochloride with the calculated quantity of hydrogen chloride in ethyl acetate, the hydrochloride then being recrystallized from isopropanol/diisopropyl ether.

The hydrochloride of the (±)-1,4,5,6-tetrahydro-6-isopropyl-2-methyl-4-phenyl-pyrido[4,3-d]pyrimidine is obtained in the form of colorless cystals with a m.p. of 296°–297° C. (decomp.).

During the above described chromatography (±)-1,4-dihydro-5-isopropoxy-2-methyl-5-oxo-4-phenyl-pyrido[4,3-d]pyrimidine ($R_f$ 0.3) is isolated as an additional product.

We claim:
1. A compound of the formula,

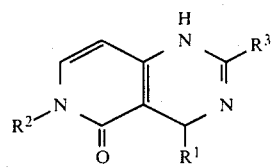

wherein $R^1$ is phenyl or phenyl substituted in the two and/or three or six position by one or more of the same or different substitutents selected from halogen, nitro, $C_1$-$C_4$ alkyl, $C_1$-$C_4$ alkoxy, difluoromethoxy, trifluoromethoxy, dimethylamino, diethylamino, methythio, trifluoromethyl and methylenedioxy $R^2$ is hydrogen, a $C_1$-$C_6$ alkyl group, a $C_1$-$C_8$ alkoxy group, or a $C_1$-$C_8$ aminoalkyl group of the formula

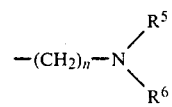

$R^5$ and $R^6$ may be the same or different and represent a straight or branched alkyl group or together form an alkylene group and n is two or three, $R^3$ is a straight or branched alkyl group having one to four carbon atoms, phenyl or phenyl substituted by one or more of the same or different substitutents selected from halogen, nitro, $C_1$-$C_4$ alkyl $C_1$-$C_4$ alkoxy, difluoromethoxy, trifluoromethoxy, dimethylamino, diethylamino, methythio, trifluoromethyl and methylenedioxy, or a pharmacologically acceptable acid addition salt thereof.

2. A compound according to claim 1, wherein
$R^1$ represents phenyl or phenyl substituted in the two, three, or six positions;
$R^2$ is a $C_1$-$C_6$ alkyl group, a $C_1$-$C_8$ alkoxyalkyl group or a $C_1$-$C_8$ aminoalkyl group; and
$R^3$ a $C_1$-$C_4$ alkyl radical or a phenyl radical.

3. A compound according to claim 1 wherein
$R^1$ represents phenyl or phenyl substituted by halogen, nitro, methyl, methoxy, difluoromethoxy, trifluoromethoxy, dimethylamino, diethylamino, methylthio, or trifluoromethyl, or phenyl disubstituted by methoxy, methylenedioxy or halogen atoms, which may be the same or different;
$R^2$ is methyl, ethyl, n-propyl, isopropyl, n-butyl, isobutyl or tert. butyl, an alkoxyalkyl group of the Formula II

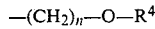

or an aminoalkyl group of the Formula III

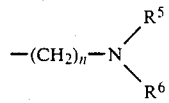

wherein $R^4$ represents a straight or branched alkyl group and $R^5$ and $R^6$ may be the smae or different and represent a straight or branched alkyl group, or together form a lower alkylene group, and n equals two or three; and $R^3$ represents methyl, ethyl, n-propyl, isopropyl, or phenyl.

4. A pharmaceutical composition comprising a vasospasmolytically effective amount of a compound according to claim 1 together with a pharmacologically acceptable carrier or or diluent.

5. A method of treating vascular diseases comprising administering to a host suffering therefrom an effective amount of a composition according to claim 4 in unit dosage form.

* * * * *